US006984659B2

(12) United States Patent
Feuerstein et al.

(10) Patent No.: US 6,984,659 B2
(45) Date of Patent: Jan. 10, 2006

(54) 2-PYRROLIDINONE DERIVATIVES SUBSTITUTED AT POSITION 4 FOR REDUCING THE EXTRACELLULAR GLUTAMATE LEVEL

(75) Inventors: Thomas J. Feuerstein, Horben (DE); Rainer Knoerle, Freiburg (DE)

(73) Assignee: Klinikum der Albert-Ludwigs Universitaet, Freiburg (DE)

( * ) Notice: Subject to any disclaimer, the term of this patent is extended or adjusted under 35 U.S.C. 154(b) by 0 days.

(21) Appl. No.: 10/108,879

(22) Filed: Mar. 29, 2002

(65) Prior Publication Data
US 2002/0173537 A1 Nov. 21, 2002

Related U.S. Application Data

(63) Continuation-in-part of application No. 09/554,587, filed as application No. PCT/EP98/07383 on Nov. 18, 1998, now Pat. No. 6,384,069.

(30) Foreign Application Priority Data
Nov. 18, 1997 (DE) ................................ 197 51 062

(51) Int. Cl.
A61K 31/40 (2006.01)
(52) U.S. Cl. ...................... 514/424; 514/408; 514/409
(58) Field of Classification Search ................ 514/409, 514/408, 424
See application file for complete search history.

(56) References Cited

U.S. PATENT DOCUMENTS 5,068,413 A * 11/1991 Steiner et al. .............. 562/507
5,319,135 A 6/1994 Jennings et al.
6,054,482 A 4/2000 Augart et al.

FOREIGN PATENT DOCUMENTS

| EP | 0 414 263 | 2/1991 |
| EP | 0 446 570 | 9/1991 |
| EP | 1 289 365 B1 | 12/2003 |
| WO | WO 97/29101 | 8/1997 |
| WO | WO 97/33858 | 9/1997 |
| WO | WO 97/33859 | 9/1997 |

OTHER PUBLICATIONS

Kearney et al. The effect of cyclodextrins on the rate of intramolecular lactamization of gabapentin in aqueous solution, 1992, International Journal of Pharmaceutics, vol. 78, pp. 25-34.*
Enders, A. et al., "Pharmacology of a new group of centrally stimulating drugs", Arzneimittel-Forschung, 1960, pp. 243-250.
Nakamura, J. et al., "Comparative Studies on the Anticonvulsant Activity of Lipophilic Derivatives of γ-Aminobutyric Acid and 2-Pyrrolidinone in Mice", J. Pharmacobio-Dyn., 1991, pp. 1-8, Vo. 14.
Reedy, P.A., et al., "3-3-Dialkyl- and 3-Alkyl-3-Benzyl-Substituted 2-Pyrrolidinones: A New Class of Anticonvulsant Agents", J. Med. Chem., 1996, pp. 1898-1906, vol. 39.
Perez De La Mora, M., et al., "Anticonvulsant effect of 5-ethyl, 5-phenyl, 2-pyrrolidione and its possible relationship to γ-aminobutyric acid-dependent inhibitory mechanisms", Biochemical Pharmacology, 1973, pp. 2635-2639, vol. 22.

(Continued)

Primary Examiner—Shengjun Wang
(74) Attorney, Agent, or Firm—Heller Ehrman LLP

(57) ABSTRACT 2-pyrrolidinone derivatives which have in position 4 at least one substituent are described herein. Methods of treating polygltamine disorders such as Huntington's disease, dentorubropallidoluysian atrophy (DRPLA), spinal and bulbar muscular atrophy (SBMA), and spinocerebellar ataxias with 2-pyrrolidinone derivatives are also descibed.

6 Claims, 8 Drawing Sheets

OTHER PUBLICATIONS

Waldmeier, P.C., et al., "Effect of carbamazepine, oxcarbazepine and lamotrigine on the increase in extracellular glutamate elicited by veratridine in rat cortex and striatum", Naunyn Schmiedeberg's Arch Pharmacol, 1996, pp. 164-172, vol. 354.

Sarbbani: Sahay Guha Sircab, "The Preparation of the Substituted Butyrolaccams", J. Ind. Chem., 1928, p. 552, vol. 5.

Siesjo, B.K., et al., "Calcium, Excitotoxins, and Neuronal Death in the Brain", Annals NY Acad. Sci, 1989, pp. 234-251, vol. 568.

Liu, H.T. et al., "NMDA-receptor regulation of substance P release from primary afferent nociceptors", Nature, 1997, pp. 721-724, vol. 386.

Bryson, H.M. et al., "Riluzole: A Review of its Pharmacodynamic and Pharmacokinetic Properties and Therapeutic Potential in Amyotrophic Lateral Sclerosis", Drug Evaluation, 1996, pp. 549-563, vol. 52.

La Spada AR, Taylor JP (2003) Polyglutamine placed into context. Neuron 38:681-684.

Bonini NM, Fortini ME (2003) Neurosci Human Neurodegenerative Disease Modeling Using Drosophila. Annu Rev 26, Epub ahead of print.

* cited by examiner

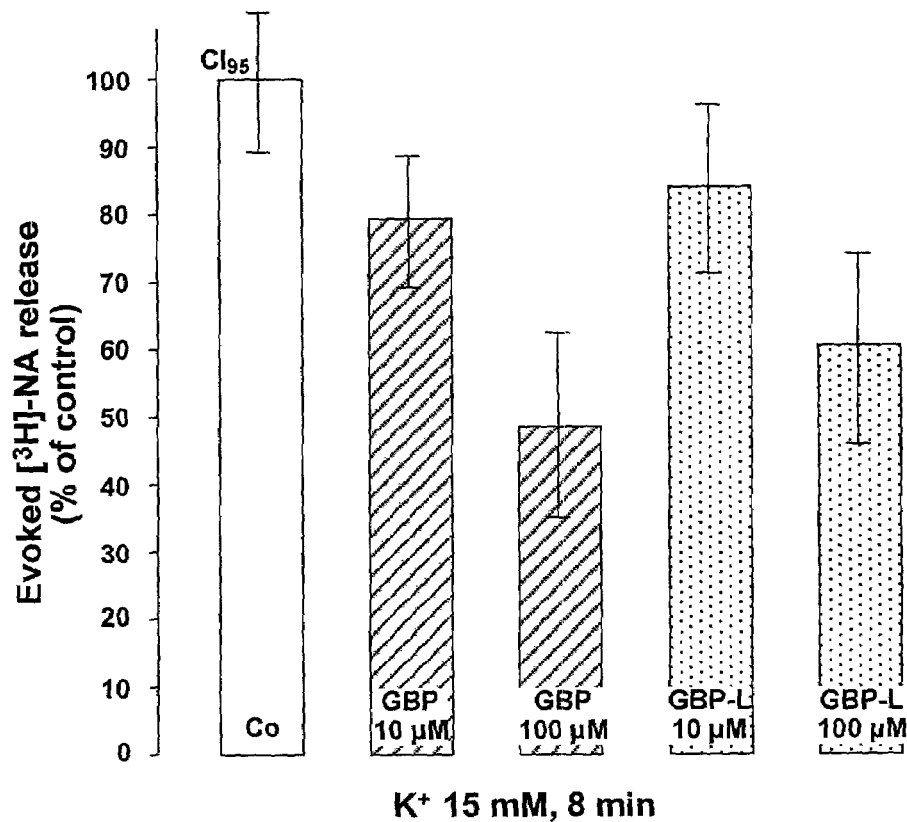
Figure 1.0

Figure 2.0
Incubation, superfusion and separation of [$^3$H]-Glu
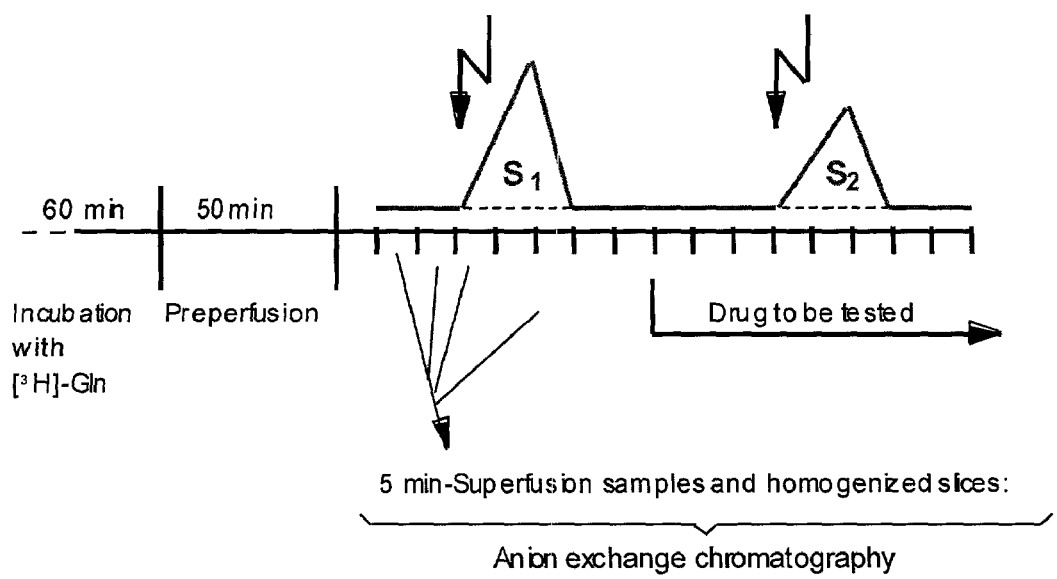

Figure 3.0
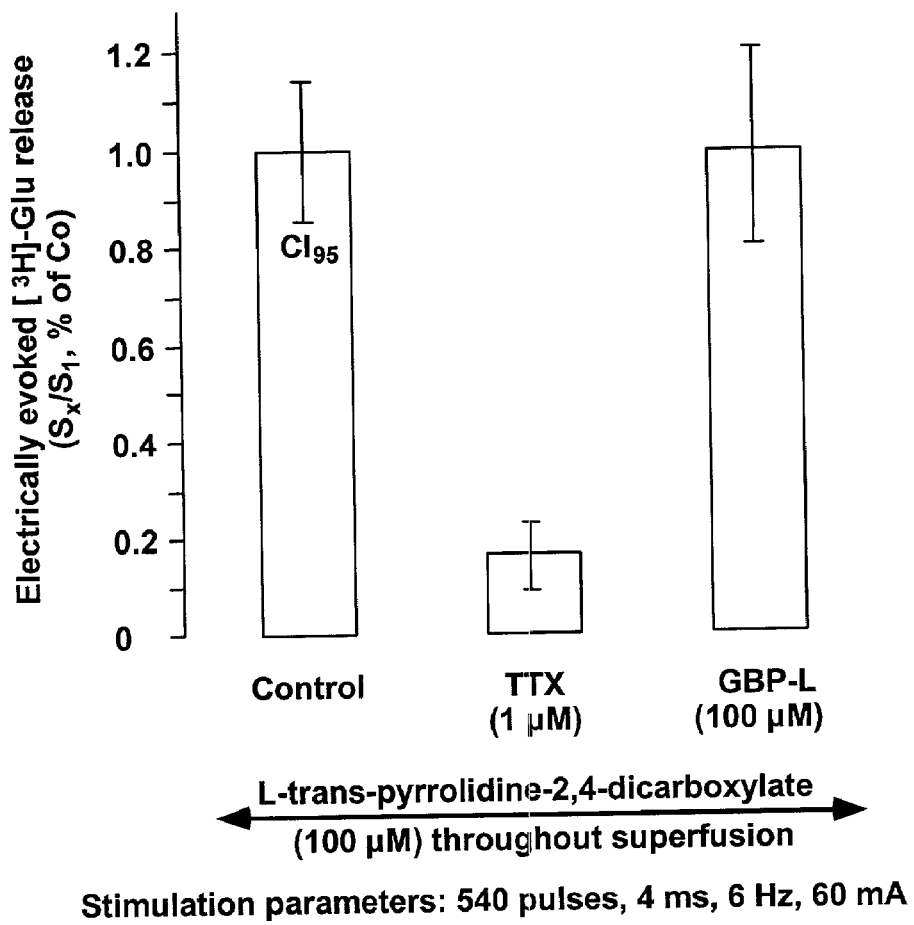

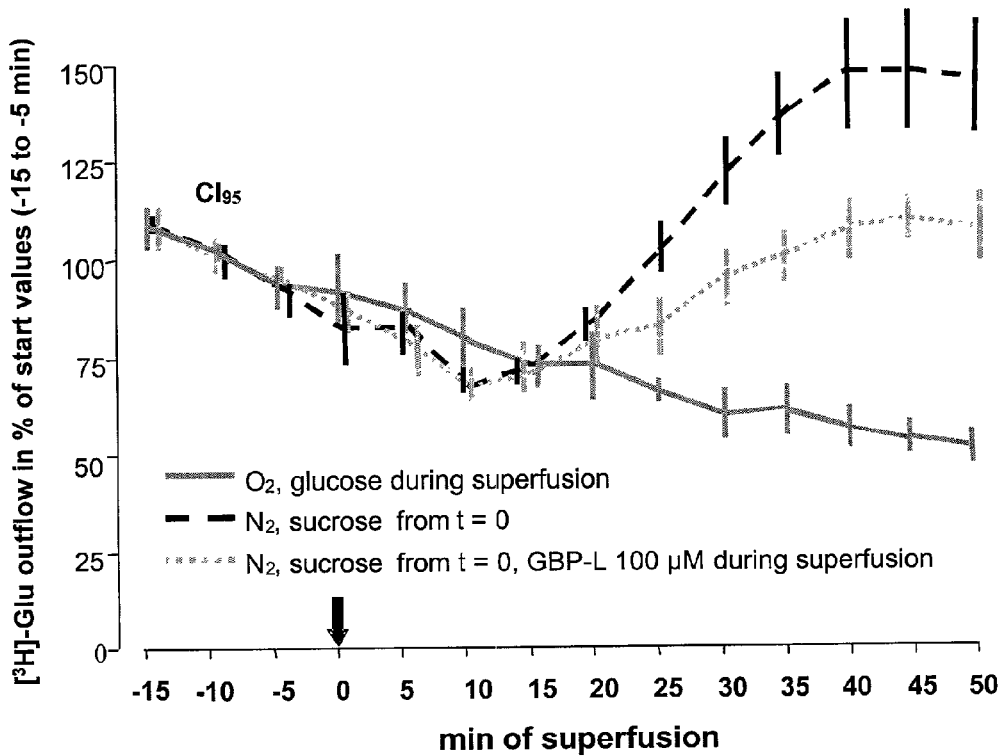
Figure 4.0
Effects of GBP-L on „ischemia"-induced [$^3$H]-Glu release from [$^3$H]-Gln-loaded hippocampal slices of the rat Figure 5.0
Effect of GBP-L in the absence and presence of glibenclamide and effect of minoxidil sulfate on the „ischemia"-induced [³H]-Glu release from rat hippocampal slices
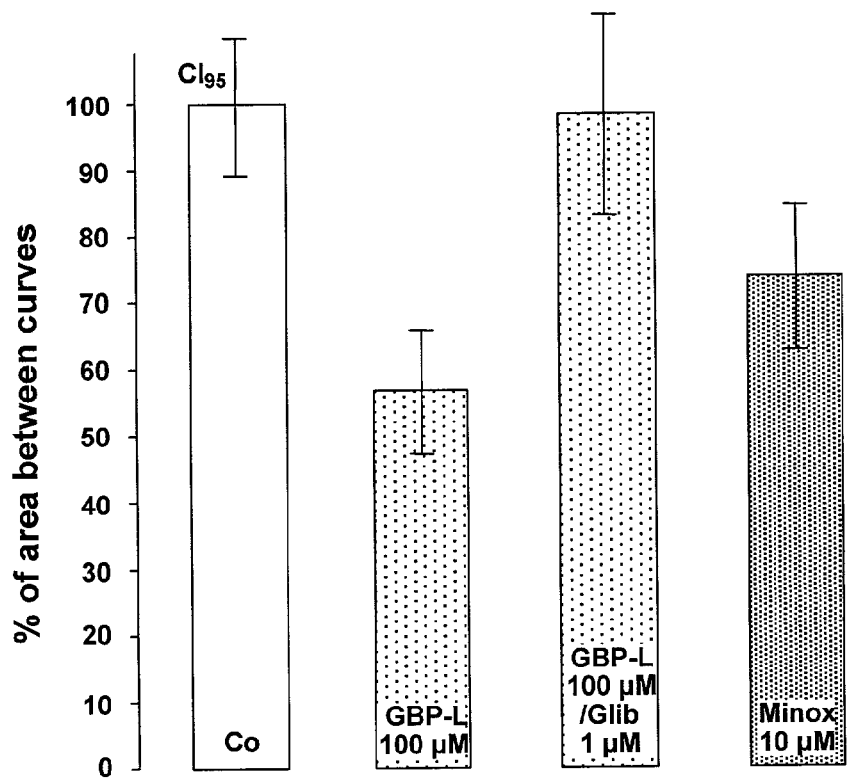

Figure 6.0
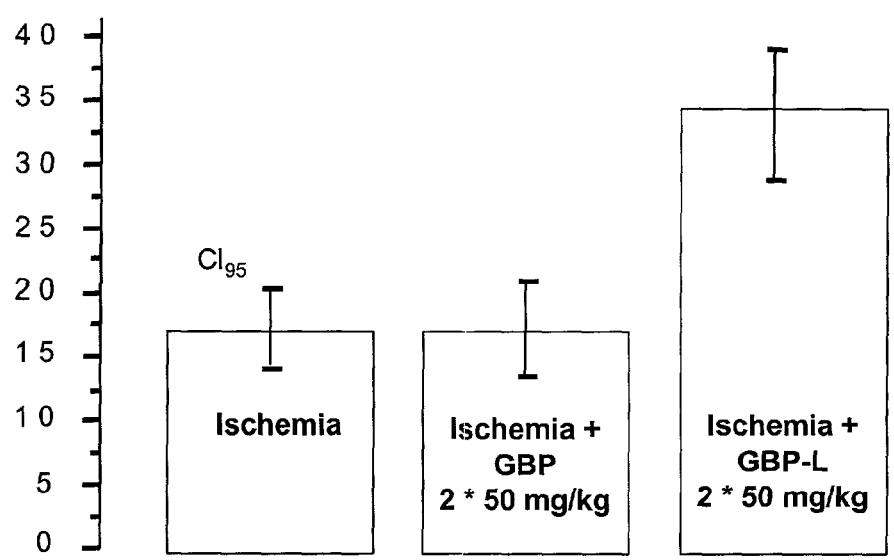

Figure 7.0
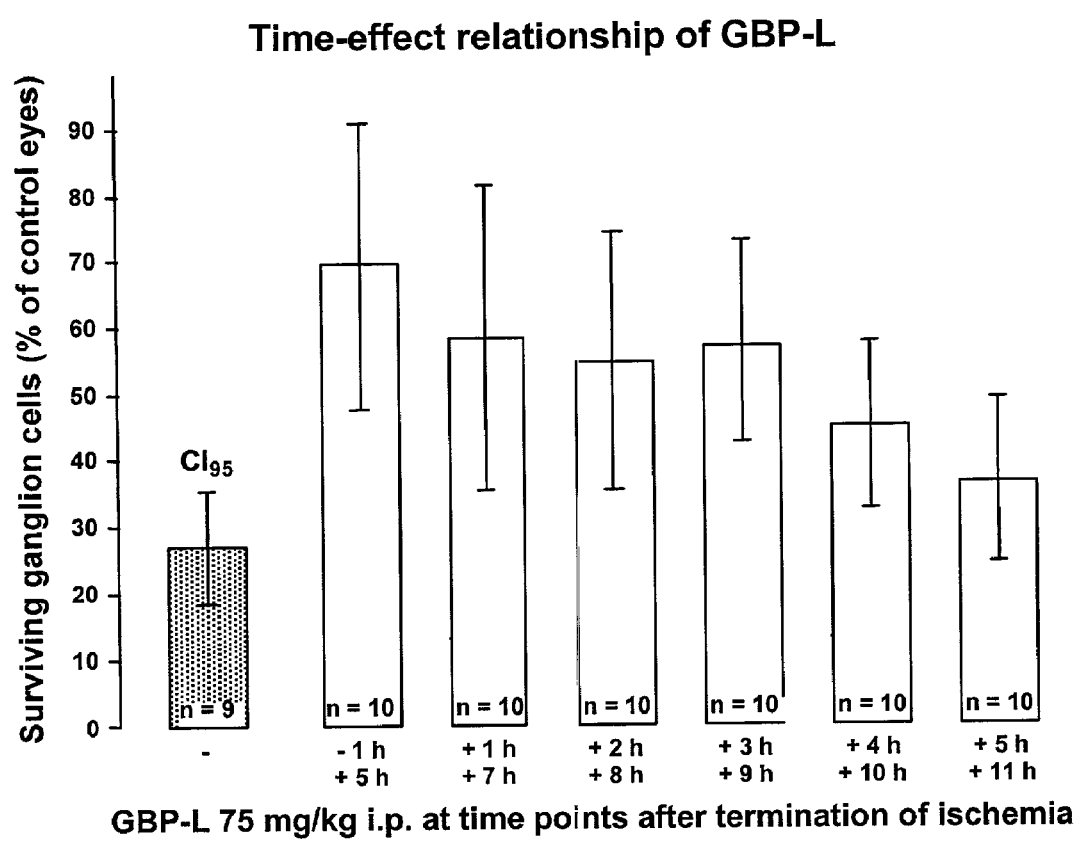

Figure 8.0
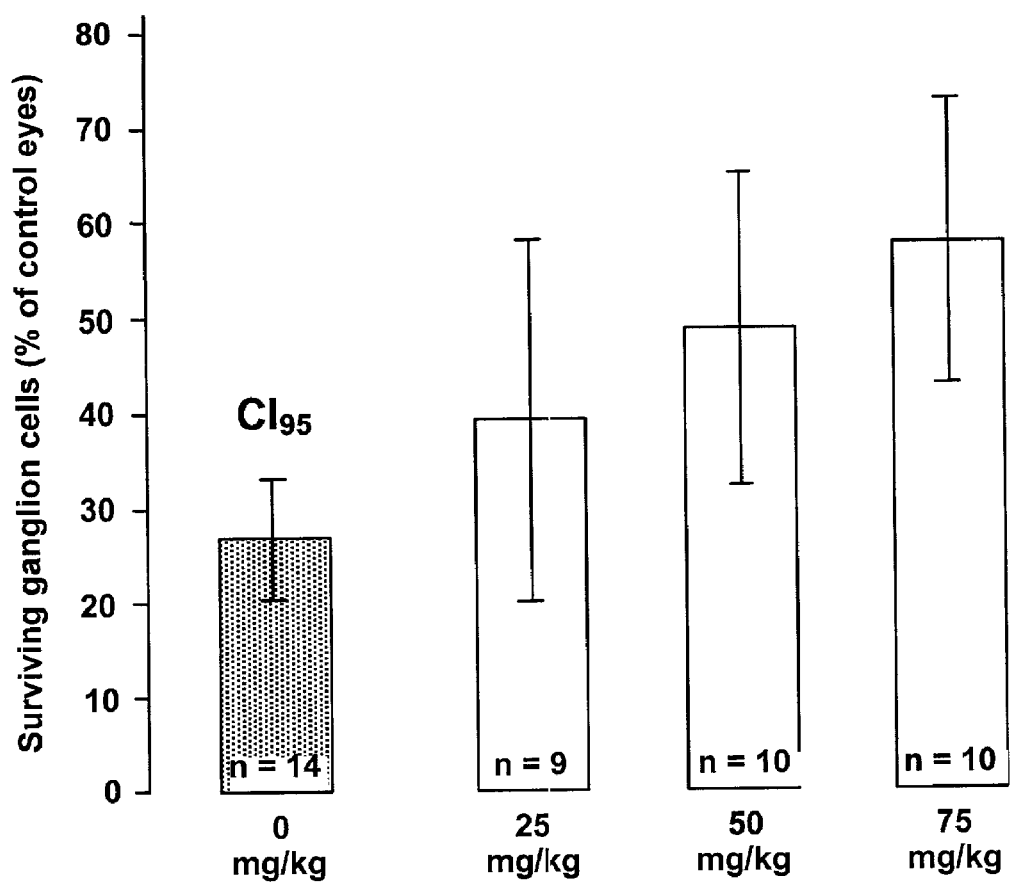

2-PYRROLIDINONE DERIVATIVES SUBSTITUTED AT POSITION 4 FOR REDUCING THE EXTRACELLULAR GLUTAMATE LEVEL

This application is a continuation-in-part of U.S. Ser. No. 09/554,587 filed Jul. 12, 2000, now U.S. Pat. No. 6,384,069, which is a 371 of PCT/EP98/07,383 filed Nov. 18, 1998, the disclosure of which is incorporated herein by reference in its entirety.

BACKGROUND OF THE INVENTION

Glutamate (Glu) is the essential excitatory transmitter in the central nervous system. High extra-cellular concentrations of Glu in the extracellular space lead to excitotoxic damage (Siesjö B K, Bengtsson F, Grampp W, Theander S, 1989, Calcium, excitotoxins, and neuronal death in the brain. Ann N Y Acad Sci 568:234–251). Examples of disorders of the central nervous system in which excitotoxicity is involved are stroke, hypoglycemia, hypoxia, trauma and epilepsy as acute disturbances, but also chronic disturbances in the sense of neurodegeneration such as Alzheimer's disease, AIDS-associated dementia, amyotrophic lateral sclerosis, Parkinson's disease, chronic alcoholism and others. In cases of chronic pain, an increased glutamatergic transmission (associated with elevated extracellular Glu concentrations) is responsible for plastic changes and is essentially involved in the pathogenesis of the "pain disorder" which is remote from the actual cause (Liu H T, Mantyh P W, Basbaum A I, 1997, NMDA-receptor regulation of substance P release from primary afferent nociceptors. Nature 386:721–724).

Huntington's disease (HD) is also associated with extra-cellular glutamate levels. Huntington's disease is a progressive, autosomal dominantly inherited, neurodegenerative disease that is characterized by involuntary movements (chorea), cognitive decline and psychiatric manifestations. Genetically, it is caused by a CAG repeat expansion, corresponding to an elongated polyglutamine segment on the protein level. Immunohistochemical studies on Huntington's disease tissue, using antibodies raised to the N-terminal region of huntingtin (the gene product with Gln repeats) and ubiquitin, have recently identified neuronal inclusions within densely stained neuronal nuclei, peri-nuclear and within dystrophic neuritic processes (McGowan et al. 2000, Amyloid-like inclusions in Huntington's disease. Neurosci 100:677–680). Nuclear inclusions formed by the disease protein area are a common pathological feature of polyglutamine diseases. The finding that nuclear inclusions are ubiquitinated suggests that alterations in the major intracellular system for degrading proteins, the ubiquitin-proteasome pathway, may be involved in the pathogenesis of polyglutamine diseases such as Huntington's disease (Morbus Huntington), dentorubropallidoluysian atrophy (DRPLA), spinal and bulbar muscular atrophy (SBMA) and spinocerebellar ataxias (SCA-1, -2, -3, -6, -7). (see Violante et al. 2001, Brain Res Bull October-November 1; 56(3–4): 169–172). An overview of chronic and acute neurodegenerative diseases which can be treated and/or prevented by compounds of the present application, including polyglutamine diseases, is given in Schinder et al., 1996, J. Neuroscience, October 1; 16(19):6125–6133.

Substances which prevent the excitotoxicity of and the plastic changes due to Glu by reducing the extracellular Glu level would be a crucial advantage for the therapy and prophylaxis of the pathological states mentioned.

Several substances which (allegedly) influence glutamatergic transmission are known or already on the market as medicines. They include the Glu-release inhibitor riluzole (Bryson H M, Fulton B, Benfield P, 1996, Riluzole. A review of its pharmacodynamic and pharmacokinetic properties and therapeutic potential in amyotrophic lateral sclerosis. Drugs 52:549–563) and lamotrigine. However, the latter does not, despite assertions to the contrary originally, act as a specific inhibitor of Glu release (Waldmeier P C, Martin P, Stocklin K, Portet C, Schmutz M, 1996, Effect of-carbamazepine, oxcarbazepine and lamotrigine on the increase in extracellular glutamate elicited by veratridine in rat cortex and striatum. Naunyn Schmiedeberg's Arch Pharmacol 354:164–172). The GABA derivative gabapentin is also said to inhibit Glu synthesis in the millimolar concentration range (Goldlust A, Su T Z, Welty D F, Taylor C P, Oxender D L, 1995, Effects of anticonvulsant drug gabapentin on the enzymes in metabolic pathways of glutamate and GABA. Epilepsy Res 22:1–11); however, these concentrations cannot be reached in vivo.

Some 1-, 3- and 5-substituted derivatives of 2-pyrrolidinone are known as substances having anti-convulsant activity and/or possibly influencing glutamatergic transmission (Nakamura J, Miwa T, Mori Y, Sasaki H, Shibasaki J, 1991, Comparative studies on the anticonvulsant activity of lipophilic derivatives of gamma-aminobutyric acid and 2-pyrrolidinone in mice. J. Pharmacobiodyn 14:1–8; Reddy P A, Hsiang B C, Latifi T N, Hill M W, Woodward K E, Rothman S M, Ferrendelli J A, Covey D F, 1996, 3,3-Dialkyl- and 3-alkyl-3-benzylsubstituted 2-pyrrolidinones: a new class of anticonvulsant agents. J Med Chem 39:1898–1906; De la Mora M P, Tapia R, 1973, Anticonvulsant effect of 5-ethyl, 5-phenyl,2-pyrrolidinone and its possible relationship to γ-aminobutyric acid-dependent inhibitory mechanisms. Biochem Pharmacol 22:2635–2639).

The publication Arzneimittelforschung 10, 1960, page 243–250 discloses in Table I No. XVII the compound

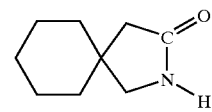

However, this compound is not regarded as particularly active, as is evident from the discussion in the righthand column on page 249 of this publication. Nor does the-publication contain any reference to the use of this compound as pharmaceutical.

At present there is no satisfactory pharmaceutical which effectively reduces the extracellular glutamate level. Even the medicines riluzole and lamotrigine, which are already commercially available, have only low activity as inhibitors of Glu release and show side effects, through metabolism or their mechanism of action, which restricts their therapeutic use.

There also still remains a need for compounds which reduce or inhibit the effects caused by polyglutamine residues and which are active against the pathogenesis of polyglutamine diseases.

SUMMARY OF THE INVENTION

It is therefore an object of the invention to provide novel medicinal substances and pharmaceuticals which are effective for disorders which are attributable to an elevated glutamate level and which can therefore be employed for the prophylaxis and treatment of disorders of the central nervous system such as stroke, hypoglycemia, hypoxia, trauma and epilepsy, Alzheimer's disease, AIDS-associated dementia, amyotrophic lateral sclerosis, Parkinson's disease and chronic alcoholism. It is intended that these novel pharmaceuticals not have the disadvantages of the pharmaceuticals disclosed in the prior art.

The pharmaceuticals are preferably able to influence glutamatergic transmission and reduce the extracellular glutamate level and/or prevent the depolarization and over-excitation of postsynaptic cells, for example by presynaptically released glutamate.

This object is achieved according to the invention by providing a subject in need thereof, with a compound of the instant invention, which is a 2-pyrrolidinone derivative of the general formula

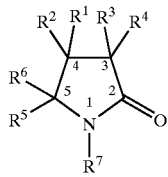

in which $R^1$ and $R^2$ are, independently of one another, hydrogen atoms, hydroxyl groups, amino groups, $C_1$–$C_{10}$ alkoxy radicals, $C_1$–$C_{10}$ alkyl radicals or $C_1$–$C_{10}$ alkylamino radicals, or $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkoxy radicals, $C_1$–$C_4$ alkoxy radicals and $C_1$–$C_4$ alkylamino radicals, with the proviso that $R^1$ and $R^2$ are not both hydrogen atoms, $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and $R^7$ is a hydrogen atom or a $C_1$–$C_{10}$ alkyl radical or $C_1$–$C_{10}$ acyl radical, pharmacologically acceptable salts thereof and prodrugs thereof for use as therapeutic active ingredient.

The alkyl radicals as well as the alkyl constituents of the alkoxy radicals and alkylamino radicals may be straight-chain or branched.

In a preferred embodiment, the invention provides a method for treating a polyglutamine disease comprising administering compounds of the instant invention. A polyglutamine disease is a neurodegerative disease generally associated with elevated extracellular glutamate.

In another preferred embodiment, the invention provides a method of treating a disease selected from the group consisting of Huntington's disease, dentorubropallidoluysian atrophy (DRPLA), spinal and bulbar muscular atrophy (SBMA), and spinocerebellar ataxias (SCA-1, -2, -3, -6, -7) comprising administering to subjects in need thereof compounds of the instant invention.

In another preferred embodiment, the invention provides a method of treating acute and chronic glaucoma comprising, administering to subjects in need thereof compounds of the instant invention.

BRIEF DESCRIPTION OF THE DRAWINGS

FIG. 1.0 Inhibitory effects of GBP (and pregabalin) in the superfusion model of potassium-evoked release of [$^3$H]-noradrenaline ([$^3$H]-NA) from rat neocortex slices.

FIG. 2.0 The experimental procedure for measuring the effect of GBP-L on Glu efflux from rat caudatoputamen slices tested in the model of [$^3$H]-glutamate ([$^3$H]-Glu) release from [$^3$H]-glutamine ([$^3$H]-Gln)-loaded slices of the rat hippocampus.

FIG. 3.0 GBP-L release model.

FIG. 4.0 The effect of GBP-L on ischemia-induced [$^3$H]-lu release from [$^3$H]-Gln-loaded hippocampal slices of the rat.

FIG. 5.0 The effect of GBP-L in the absence and the presence of glibenclamide and the effect of minoxodil sulfate on the ischemia-induced [$^3$H]-Glu release from rat hippocampal slices.

FIG. 6.0 % of surviving neurons in the ischemic eye.

FIG. 7.0 The time-effect relationship of GBP-L.

FIG. 8.0 The dose dependence of the neuroprotective effect of GBP-L.

DETAILED DESCRIPTION OF THE PREFERRED EMBODIMENT

It has been found, surprisingly, that 2-pyrrolidinone derivatives which have in position 4 at least one substituent as deied above have an excellent effect in reducing the extracellular glutamate level and can therefore be used for the prophylaxis and treatment of disorders of the central nervous system such as stroke, hypoglycemia, hypoxia, trauma and epilepsy, Alzheimer's disease, AIDS-associated dementia, amyotrophic lateral sclerosis, Parkinson's disease and chronic alcoholism. The compounds may likewise preferentially prevent depolarization and over-excitation of postsynaptic cells, for example by presynaptically released glutamate. It has also been found that the instant 2-pyrrolidinone derivatives which have in position 4 at least one substituent are particularly useful in treating polyglutamine diseases such as Huntington's disease, dentorubropallidoluysian atrophy (DRPLA), spinal and bulbar muscular atrophy (SBMA), and spinocerebellar ataxias (SCA-1, -2, -3, -6, -7). Substitution of the 2-pyrrolidinone derivatives according to the invention in positions 3 and 5 of the pyrrolidinone ring is substantially uncritical as long as substitution in position 4 of the pyrrolidinone ring is ensured. Preferred 2-pyrrolidinone derivatives are unsubstituted in positions 3 and 5 or have one or two alkyl substituents with up to 10 carbon atoms, preferably up to 6 carbon atoms and/or one or two aryl substituents with 6 to 10 carbon atoms, preferably phenyl groups.

Substitution on the nitrogen atom of the 2-pyrrolidinone derivatives is also substantially uncritical, but the nitrogen atom of the 2-pyrrolidinone derivatives according to the invention is preferably unsubstituted or substituted by a $C_1$–$C_6$ alkyl radical or a $C_1$–$C_6$ acyl radical.

The substitution at position 4 of the pyrrolidinone ring is essential for the 2-pyrrolidinone derivatives according to the invention. It is therefore necessary for at least one of the radicals $R^1$ and $R^2$ to be different from hydrogen. One of the radicals $R^1$ and $R^2$ is preferably a hydrogen atom, and other radical is preferably a $C_1$–$C_{10}$ alkyl radical, particularly preferably a $C_1$–$C_6$ alkyl radical.

If the radicals $R^1$ and $R^2$ are different, as in the particularly preferred embodiment of the invention described above, the claimed 2-pyrrolidinone derivatives show optical isomerism. The invention relates both to the pure R and to the pure S form of the pyrrolidinone derivatives, but also to any racemic mixtures of the R and S forms.

It is particularly preferred according to the invention for the radicals $R^1$ and $R^2$ to form, together with the carbon atom in position 4 of the pyrrolidinone ring, a saturated or unsaturated 5- to 10-membered ring. This ring may have up to two heteroatoms selected from oxygen, sulfur and nitrogen atoms and be unsubstituted or substituted by up to three substituents selected from hydroxyl groups, amino groups, $C_1$–$C_4$ alkyl radicals, $C_1$–$C_4$ alkoxy radicals and $C_1$–$C_4$ alkylamino radicals. However, the radicals $R^1$ and $R^2$ preferably form an unsubstituted ring which preferably has no heteroatoms, is preferably saturated and particularly preferably consists of six carbon atoms, including the carbon atom in position 4 of the 2-pyrrolidinone ring. A particularly preferred 2-pyrrolidinone derivative of the invention is 8-azaspiro[5,4]decan-9-one (gabapentin lactam).

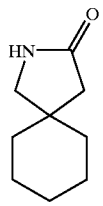

Where at least one of the radicals $R^3$, $R^4$, $R^5$ and $R^6$ is different from hydrogen, structural isomers also occur in addition to the optical isomers (to which the invention relates). All structural isomers and their mixtures are included among the 2-pyrrolidinone derivatives according to the invention.

Instead of the 2-pyrrolidinone derivative as defined above, it is also possible to use pharmacologically acceptable salts, in particular acid addition salts, of the 2-pyrrolidinone derivative. It is likewise possible to use a pharmaceutical precursor (prodrug) of the 2-pyrrolidinone derivatives according to the invention as therapeutic active ingredient. Such a prodrug means a compound which is not itself pharmacologically active but which is converted after administration to a patient in vivo into an active 2-pyrrolidinone derivative as defined above.

The compounds according to the invention can be prepared in a manner known per se. Thus, the 8-azaspiro[5,4]decan-9-one which is particularly preferred according to the invention is already described in the literature (Kearney A. S., Mehta S. C., Radebaugh G. W. The effect of cyclodextrins on the rate of intra-molecular lactamization of gabapentin in aqueous solution. International Journal of Pharmaceutics, 78 20 (1992), 25–34, and the reference, which has already been discussed above, Arzneimittelforschung 10, 1960, pages 243–250), but there is no proposal that this compound be used as therapeutic active ingredient. The 8-azaspiro[5,4]decan-9-one which is preferred according to the invention can be regarded as lactam of the known compound gabapentin and be prepared, for example, by irradiation of a phosphate-buffered aqueous gabapentin solution with ultraviolet light. Substituted derivatives of 8-azaspiro[5,4]decan-9-one can be prepared by lactamization of appropriately substituted gabapentin derivatives. Preferred derivatives are those having a $C_1$–$C_4$ alkyl radical, a halogen, a hydroxyl group or an amino group, preferably a $C_1$–$C_4$ alkyl radical or a halogen atom.

The compound can also be prepared in accordance with the following scheme.

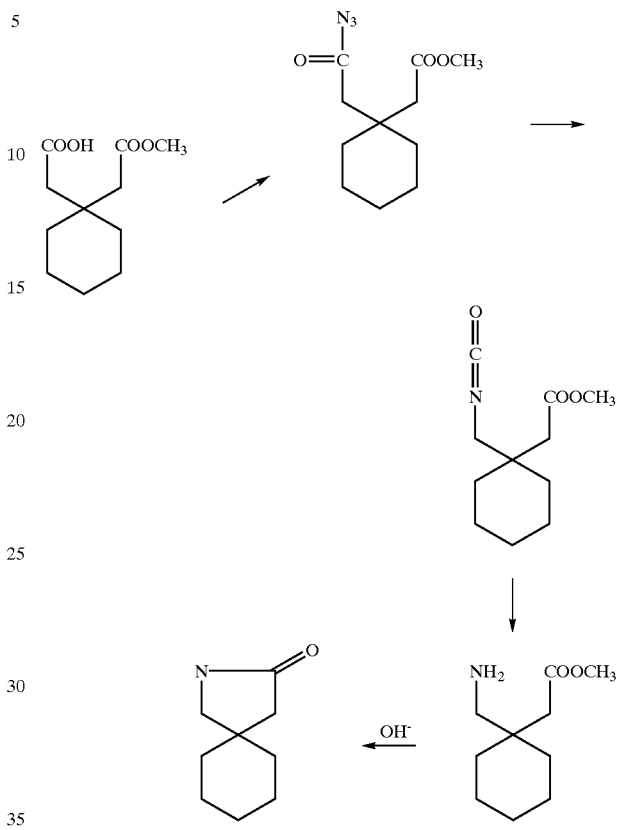

1,1-Cyclohexanediacetic acid monomethyl ester is converted via the corresponding acid chloride into the azide. The azide is degraded by the Curtius method to the isocyanate. The isocyanate is then hydrolyzed to give methyl 1-aminomethyl-1-cyclohexaneacetate. Heating this substance in alkaline methanol under reflux for three days affords 8-azaspiro[5,4]decan-9-one or gabapentin lactam. GBP-L was characterized by means of Thin Layer Chromatography, Infrared-Spectroscopy, [$^1$H]-NMR and [$^{13}$C]-NMR (Nuclear Magnetic Resonance Spectroscopy) and FAB-MS (Fast Atom Bombardment Mass Spectroscopy).

A general synthetic method for the 4-substituted 2-pyrrolidinones according to the invention starts, based on the synthesis of 3-substituted GABA derivatives published by Andruszkiewicz and Silverman (R. Andruszkiewicz and R. B. Silverman, Synthesis 953–955 (1989)) from appropriately substituted α,β-unsaturated carboxylic esters (1) which can be obtained inter alia by a Reformatzky reaction. After reaction with nitromethane, a Michael addition results in a nitro compound (2) which is converted by reduction with elemental hydrogen into the corresponding amino compound (3). After ester cleavage and activation of the carboxylate function by a good leaving group (for example conversion into the carbonyl halide), the corresponding 4-substituted 2-pyrrolidinone is obtained by cyclization.

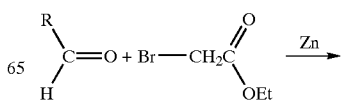

-continued

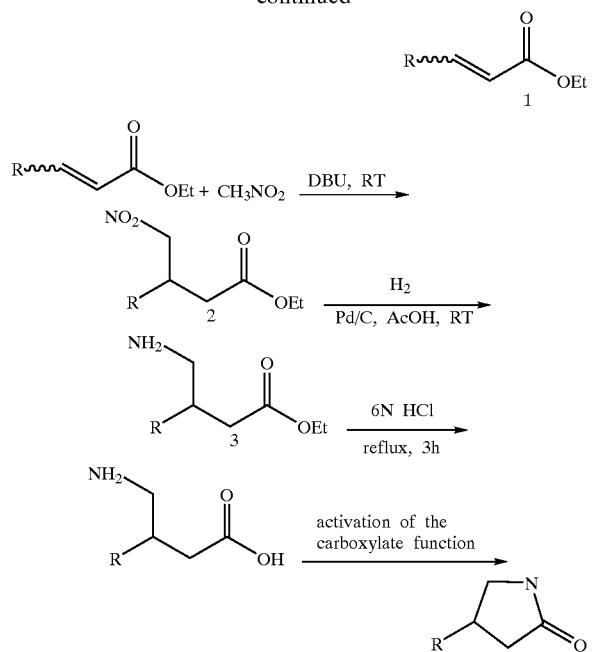

The compositions according to the invention can be formulated in a manner known per se to give the pharmaceuticals for mammals, preferably humans. The compositions according to the invention are present in the pharmaceuticals mixed with an organic or inorganic pharmaceutical carrier suitable for enteral or parenteral administrations. Oral administration of the compositions according to the invention by way of tablets, capsules, powders or in liquid form, such as suspensions, in solution, as emulsion or as syrup is particularly preferred.

When formulated as tablets, conventional pharmaceutical carriers are used, such as sodium citrate, lactose, microcrystalline cellulose and starch, lubricants such as anhydrous silica, hydrogenated castor oil, magnesium stearate, sodium lauryl sulfate and talc, and binders such as starch paste, glucose, lactose, gum arabic, mannitol, magnesium trisilicate and talc. If the compositions according to the invention are to be administered by way of liquids it is possible to use conventional liquid carriers.

Formulation for injections and infusions or as suppositories is likewise possible, as is known in the specialist area and described in relevant standard works.

The compositions according to the invention can likewise be formulated in a manner known per se as depot formulations or to give pharmaceuticals with delayed or retarded release.

The dose form of the compositions according to the invention depends on the specific composition and other factors and can be determined by a skilled worker on the basis of the condition of the patient to be treated, the severity and nature of the disease to be treated, possible side effects of the compounds etc.

An effective amount is that amount which corresponds to a decrease in extracellular glutamate or an alleviation of symptoms subsequent to elevated extracellular glutamate. Similarly, treating refers to a decrease in extracellular glutamate or an alleviation of symptoms subsequent to extracellular glutamate. The dosage for a specific patient is dependant on the age, body weight, general health conditions, sex, diet, dose interval, administration routes, excretion rate, combinations of drugs. Both the effective amount and the dosage are well within the skill of the artisan.

The examples illustrate the invention.

EXAMPLES

Example 1

A solution of gabapentin (100 $\mu$M) in physiological buffer (composition below) with a pH of 7.4 was prepared and irradiated with ultraviolet light (260 and 330 nanometers) at 37° C. for two hours. As described in Kearney A. S. et al., International Journal of Pharmaceutics, 78 (1992), 25–34, this slowly produces the lactam 8-azaspiro[ 5,4]decan-9-one. Because of the slow reaction rate, a yield of about 1% is assumed in accordance with Kearney et al. (1992), which corresponds to a 1 $\mu$M solution.

The activity of this solution in reducing the extracellular glutamate level was shown by means of superfusion experiments on rat brain slices. Slices with a thickness of 350 $\mu$m from the rat striatum were used for this. In each case, two slices were employed in a superfusion chamber with an extremely small dead volume, about 100 $\mu$l. Physiological buffer (concentrations in mM: NaCl 121, KCl 1.8, $CaCl_2$, 1.3, $MgSO_4$ 1.2, $NaHCO_3$ 25, $KH_2PO_3$ 1.2, glucose 11, pH 7.4, 95% $O_2$/5% $CO_2$-saturated) is then passed over them at 37° C. After a preliminary perfusion, which serves in particular to remove tissue particles and amino acids released by the injury to the tissue, superfusate fractions are collected at a flow rate of 400 to 800 $\mu$l every five minutes. Six of the 12 chambers available are continuously flushed from the start of the preliminary perfusion with an approximately 1 $\mu$M solution of 8-azaspiro[5,4]decan-9-one, and the remaining chambers which are flushed with buffer serve as control. The superfusates obtained are filtered (0.45 $\mu$m pore size) and the amino acid concentrations are determined by HPLC.

Details of the method are described, for example, in R. Knörle et al., Neuroscience Letters 221 (1997), 169–172.

The results show a marked reduction in the extracellular glutamate concentration due to the 8-aza-spiro[5,4]decan-9-one. With the samples containing the compound according to the invention, 0.12 $\mu$M glutamate, $CI_{95}$=[0.10, 0.13] was found, whereas in the control tests 0.24 $\mu$M glutamate, $CI_{95}$=[0.19, 0.29] was found.

Example 2

The neuroprotective effect of the compounds according to the invention was demonstrated in vivo on the basis of the publication in Invest Ophthalmol Vis Sci 39: 1063–1066, 1998. The following results were found:

10 rats were treated with 0.9% NaCl i.p. at the start of a unilateral one-hour intraocular pressure increase. After 6 hours, the treatment was again carried out with 0.9% NaCl i.p. After 14 days, the rats were sacrificed, and the retinal gangliocytes were investigated. Compared with the respective control eye, only 17.4% (±4%) of the retinal gangliocytes had survived. The rats behaved completely normally in the 14 days after the test, and no animal died.

In the test group, likewise of 10 rats, 50 mg/kg 8-azaspiro [5,4]decan-9-one was administered i.p. at the start of a unilateral one-hour intraocular pressure increase. The compound was administered again in a dose of 50 mg/kg 6 hours after the intraocular pressure increase. After 14 days, the rats were sacrificed, and the retinal gangliocytes were investigated. It emerged that, compared with the respective control eye, 35% (±7%) of the retinal gangliocytes survived. The rats behaved completely normally in the 14 days after the test, and no animal died.

This test clearly shows the increase in the surviving retinal gangliocytes after pressure-induced retinal ischemia from 17.4% (±4%) to 35.0% (±7%). The neurodegeneration in this glaucoma model is based on an NMDA receptor-mediated Glu toxicity.

Example 3

It was possible to show in another in vitro test that the antiischemic mechanism of action of the compounds according to the invention is based on a reduction in the released Glu.

Rat hippocampus slices 350 μm thick were incubated in 3 ml of medium at 37° C. for 60 minutes. The medium contained 2 μM [$^3$H]-Gln to label the endogenous Gln pool. The slices then synthesized Glu. The slices were washed and then exposed to superfusion with a buffer for 50 minutes. At 5-minute intervals, [$^3$H]-Glu was extracted by anion exchange chromatography from a total of 15 superfusion samples and was measured by liquid scintillation counting. The fractional rates of [$^3$H]-Glu release were calculated from the [$^3$H]-Glu extracted from the superfusion samples and from the tissue slices after the superfusion.

Gabapentin lactam was first investigated in a model in which the release was induced by electrical stimulation. The release in this model responds both to tetrodotoxin and to extracellular $Ca^{++}$ ions. After the incubation with tritiated Gln, the slices were exposed to a superfusion and electrically stimulated twice, employing 540 pulses of 4 ms, 6 Hz and 60 mA. The superfusion was carried out at room temperature, not at 37° C. In addition, 100 μM of the Glu uptake blocker PDC was present so that renewed uptake of released Glu is reduced. TTX or gabapentin lactam was added from 15 minutes before the second stimulation onward. It was found that electrically induced release of Glu is partly inhibited by TTX, but not by gabapentin lactam. The quasiphysiological release of Glu is therefore not influenced by gabapentin lactam.

The model of endogenously produced [$^3$H]-Glu was likewise used to generate ischemic conditions in vitro. To make a slice "quasi ischemic", oxygen and glucose were replaced by nitrogen and sucrose during the superfusion. Sucrose was used in place of 11 μM glucose in order to maintain the osmolarity of the superfusion fluid. It is known that sucrose cannot be cleaved in vitro to glucose and fructose. Unlike the tests in which the [$^3$H]-Glu release was induced electrically, and in order to simulate an ischemia as well as possible, the [$^3$H]-Glu release was carried out during the incubation and superfusion at 37° C. It was found that the usual high concentration of the Glu uptake inhibitor PDC, namely 100 μM, noticeably reduced the response to the ischemia. All the tests were therefore carried out in the presence of only 3 μM PDC, which markedly increased the effect of the ischemia.

It was found that in this in vitro ischemia model, gabapentin lactam reduces the neurotoxic [$^3$H]-Glu output significantly.

The compounds thus unambiguously prevent in vitro the large increase in extracellular tritium-Glu in rat hippocainpus slices (previously loaded with tritium-glutamine) after replacement of $O_2$ by $N_2$ and of glucose by sucrose, specifically by about 50%. The quasiphysiological action potential-mediated Glu release was, however, unaffected by gabapentin lactam.

Comparative Example 1

Example 1 was repeated with the modification that the gabapentin-containing solution was not irradiated with ultraviolet light but was used directly in the test. The comparative solution thus contains exclusively gabapentin but no 8-azaspiro[5,4]decan-9-one. In the corresponding tests, no difference could be found between the samples treated with the gabapentin solution and the comparative samples.

Comparative Example 2

Example 2 above was repeated but employed instead of 8-azaspiro[5,4]decan-9-one the structurally similar compound gabapentin. It emerged that gabapentin showed no protective effect whatever against neurodegeneration in this glaucoma model.

Example 4

Effects of Gabapentin-Lactam in a Mouse Model of Huntington's Disease

GBP-L stands for gabapentin-lactam which is 8-aza-spiro [5,4]decan-9-one.

GBP stands for gabapentin.

Mice transgenic for exon 1 of the human HD gene (line R 6/2), carrying $CAG_{n=115-156}$ expansions, develop pronounced neuronal intranuclear inclusions, containing the proteins huntington and ubiquitin prior to the characteristic neurological phenotype with bradykinesia and seizures corresponding to the juvenile type of HD (Davies et al. 1997). The life time of these mice is up to 17 weeks. It was investigated whether gabapentin (GBP) and its derivative gabapentin-lactam (GBP-L, Jehle et al. 2000), may exert neuroprotective effects by using a battery of behavioral tests selected to measure motor aspects of fore-and hindlimb coordination and balance. In a first series of experiments mice were treated with GBP-L (100 mg/kg*day, 8 mice) and vehicle only (B mice) from the 6th week of their life until death using Alzet pumps implanted subcutaneously and delivering the test compounds systemically and continuously for up to four weeks. Empty Alzet pumps were repeatedly replaced. Animals were tested twice weekly by walking on a balance beam (width: 5 and 14 mm, Carter et al. 1999) up to week 15.5. A second series of experiments involved mice again treated with GBP-L (100 mg/kg*clay, 7 mice) and mice treated with GBP (100 mg/kg*day, 8 mice) from the 6th week of their life until death with week 17 being the maximum endpoint. In addition, immunohistochemical studies, using a monoclonal mouse antibody raised against ubiquitin, were done to analyse areas of ubiquitinated nuclear inclusions in three brain regions (hippocampus, neocortex and striatum) in a blinded fashion in order to compare mice treated with GBP-L or GBP.

In the first set of experiments, GBP-L markedly and significantly improved the motor abilities of mice compared to vehicle animals (solvent carrier). This effect (E), as measured by the time necessary to pass the balance beam, was evaluated in each single mouse according to the function $E = be^{a \cdot time}$, yielding individual graphs with parameter estimates for a and b. The area under the curve, representing the motor ability of an individual mouse, was weighted by the life of this mouse. For instance, the area under the curve of a mouse which died at week 12.5 was divided by the ratio 12.5/15.5 in order to allow for possibly different life times of the mice. The mean weighted area, representing the motor ability on the 5 mm beam, in the group treated with GBP-L was 26.64, $CI_{95}$=[17.77, 35.52], as opposed to 44.60, $CI_{95}$=[31.51, 57.69] in the vehicle group. Corresponding values of the motor ability on the 14mm beam were 17.16, $CI_{95}$=[5.25, 29.08], as opposed to 31.54, $CI_{95}$=[18.63, 44.56]. A two-way ANOVA yielded a highly significant effect on the treatment (GBP-L or vehicle, p= 0.003) and also a significant effect of the width of the beam (p=0.03). Interactions between treatment and width of the beam were insignificant (p=0.72).

The second series of experiments yielded a clear superiority of GBP-L to GBP: The mean weighted area, representing the motor ability on the 5 mm beam, in the group treated with GBP-L was 43.75, $CI_{95}$=[25.89, 61.60], as opposed to 77.33, $CI_{95}$= [53.80, 100.86] in the GBP group. The motor ability on the 14 mm beam was 30.46, $CI_{95}$=[17.31, 43.61] for GBP-L, as opposed to 65.71, $CI_{95}$=[23.22, 108.20]. Note that the observation period of the second series of experiments was 17 instead of 15.5 weeks only in the first set. Accordingly, the weighting by the life time now used the divisor 17 Instead of 15.5. The two-way ANOVA again yielded a highly significant effect of the treatment (GBP-L or GBP, p=0.007). The effect of the width of the beam was no longer significant (p=0.30), as were interactions between treatment and width of the beam (p=0.94).

Immunohistochemical studies showed a markedly and significantly reduced area of neuronal intranuclear inclusions in the hippocampus, striatum and neocartex in frozen brain sections of mice treated with GBP-L compared to GBP mice. Three mice per group were evaluated. The mean regional area of neuronal intranuclear inclusions was calculated ($\mu m^2$) for each mouse. These means were compared between regions and between treatment groups. A two-way ANOVA yielded a marked and highly significant effect of treatment (GBP-L or GBP, p=0.001). Inclusion areas of regions were not significantly different within the treatment groups (p=0.10). The mean regional areas were

| Mouse-No (GBP-L-treated): | 459 | 461 | 141 |
| --- | --- | --- | --- |
| mean hippocampal areas: | 4.47 | 4.01 | 3.61 |
| mean striatal areas: | 3.52 | 4.20 | 3.83 |
| mean neocortical areas: | 3.70 | 2.96 | 2.65 |
| Mouse-No (GBP-treated): | 441 | 441 | 479 |
| mean hippocampal areas: | 8.78 | 8.93 | 8.26 |
| mean striatal areas: | 6.43 | 7.27 | 3.84 |
| mean neoccortical areas: | 5.91 | 5.94 | 9.60 |

In summary, these results suggest a clear neuroprotective effect of GBP-L, as evident by reduced areas of intranuclear neuronal inclusions. Functionally, GBP-L improved motor abilities in the present disease model.

Example 5

Experiments with GBP-L In Vitro

Noradrenaline Release

Results on the inhibitory effects of GBP (and pregabalin) in the superfusion model of potassium-evoked release of [$^3$H]-noradrenaline ([$^3$H]-NA) from rat neocortex slices indicate that these drugs are agonists at $K_{ATP}$ channels (Freiman et al. 2001) (FIG. 1.0). The effects of GBP and GBP-L were compared by a very similar approach using rat and human neocortical slices.

Both GBP and GBP-L inhibited similarly the evoked [$^3$H]-NA release not only in the rat (not shown in FIG. 1.0), but also in human neocortex. Note that the deviations indicate confidence intervals ($CI_{95}$), not standard errors. In this model, GBP and its lactam seem equipotent. GBP and GBP-L are ineffective on the quasi-physiological, electrically evoked release of [$^3$H]-NA from both rat and human brain slices (not shown).

Glu Release

The effect of GBP-L on Glu efflux from rat caudatoputamen slices (see FIG. 1) was tested in the model of [$^3$H]-glutamate ([$^3$H]-Glu) release from [$^3$H]-glutamine ([$^3$H]-Gln)-loaded slices of the rat hippocampus. This is relevant for ischemia-related events.

The utility and the advantage of this model is that it reflects the predominant intraneuronal formation of Glu from Gln or, in other words, that measured [$^3$H]-Glu mainly represents efflux from the neuronal Glu pool since Gln serves as the major precursor of Glu in glutamatergic nerve endings (Bradford et al. 1978). The experimental procedure in brief is shown in FIG. 2.0.

Slices of 350 $\mu$m thickness were incubated at 37° C. for 60 min in 3 ml medium containing 2 $\mu$M [$^3$H]-Gln in order to label endogenous Gln pools. These slices subsequently were synthesizing Glu. The slices were washed and then superfused for 50 min with buffer. [$^3$H]-Glu was extracted from 15 5-min-superfusion samples and from the slices by anion-exchange chromatography and measured by liquid scintillation counting. Fractional rates of [$^3$H]-Glu release were calculated from extracted [$^3$H]-Glu in the superfusion samples and in the tissue slices obtained after superfusion.

Release of [$^3$H]-Glu can be elicited in different ways. The most physiological method is probably the release induction by electrical stimulation since the electrically evoked release is sensitive to tetrodotoxin (TTX), i.e. mediated by action-potentials.

GBP-L was first tested in the release model set forth in FIG. 3.0.

After incubation with tritiated Gln the slices were superfused and twice stimulated electrically with the stimulation parameters indicated. Superfusion was performed at room temperature, not at 37° C., and in the presence of 100 $\mu$M of the Glu-uptake blocker L-trans-pyrrolidine-2,4-dicarboxylate (PDC) in order to reduce the reuptake of released Glu and, thereby, to accentuate the evoked [$^3$H]-Glu signal measured in the superfusates above the basal [$^3$H]-Glu outflow. TTX or GBP-L was given from 15 min before the second stimulation onwards. The electrically evoked release of Glu was widely inhibited by TTX, but not by GBP-L. Thus, the quasi-physiological release of Glu seems not to be influenced by GBP-L. The electrically evoked release of Glu was also dependent on extracellular $Ca^{++}$, indicating exocytotic release.

To reproduce in vitro ischemic conditions the model of endogenously formed [$^3$H]-Glu was also used. To make a slice "quasi-ischemic", oxygen was replaced by nitrogen and glucose was replaced by sucrose during superfusion. Sucrose was used instead of glucose in order to maintain the osmolarity of the superfusion fluid without being cleaved into glucose and fructose in vitro. At variance to the experiments on electrically evoked [$^3$H]-Glu release and in order to mimic ischemia as close as possible the experiments on ischemia-induced [$^3$H]-Glu release were performed at 37° C. throughout incubation and superfusion. Since the usual high concentration of the Glu uptake inhibitor PDC, namely 100 μM, diminishes the response to ischemia markedly, all the following experiments were performed in the presence of only 3 μM PDC. Experiments without any uptake blocker yielded a generally lower [$^3$H]-Glu efflux.

The effect of GBP-L on ischemia-induced [$^3$H]-Glu release from [$^3$H]-Gln-loaded hippocampal slices of the rat is shown in FIG. 4.0. The broken line with small intervals represents the normal outflow in the presence of oxygen and glucose of [$^3$H]-Glu from the hippocampal slices over time. When oxygen was replaced by nitrogen and glucose was replaced by sucrose al the time point "zero" then, after about 15 min, the outflow of [$^3$H]-Glu increased markedly (solid line). When, however, GBP-L was present this increase was clearly diminished (broken line with large intervals). The highly significant reduction of the area between the broken lines with small and large intervals and the solid line from time point t=15 min amounted to 42.5%, CI$_{95}$= [33.4%, 51.5%]. The effect of GBP-L, was completely abolished by glibenclamide (1 μM), a well-known antagonist of K$_{ATP}$ channels (Jehle et al. 2000).

In additional experiments, the in vitro ischemia was terminated after 50 min by replacing nitrogen plus sucrose with oxygen plus glucose again. The elevated [$^3$H]-Glu levels returned to basal levels within 10 min, indicating reversibility of the ischemia-induced [$^3$H]-Glu efflux.

To mimic the effects of GBP-L and to stress the relevance of K$_{ATP}$ channels in this in vitro model of ischemia, minoxidil sulfate as well-known agonist of K$_{ATP}$ channels was also tested. Also this drug (10 μM) significantly reduced ischemia-induced [$^3$H]-Glu efflux.

The effect of GBP-L in the abseice and the presence of glibenclamide and the effect of minoxodil sulfate on the ischemia-induced [$^3$H]-Glu release from rat hippocampal slices is shown in FIG. 5.0.

In addition to minoxidil sulfate, also GBP itself was tested in the in vitro ischemia model since GBP had already shown efficacy as K$_{ATP}$ channel agonist in the above mentioned model of K$^+$-evoked [$^3$H]-NA release in rat and human neocortical slices. GBP (100 μM) diminished the ischemia-induced [$^3$H]-Glu efflux by 35.5%, CI$_{95}$ =[10.3%, 61.2%].

To assess the potency of glibenclamide concentration-inhibition curves of GBP-L on ischemia-induced [$^3$H]-Glu efflux were obtained in the absence and presence of 0.1 μM glibenclamide (see Jehle et al. 2000). As expected, glibenclamide shifted the concentration-response curve of GBP-L to the right, increasing the EC$_{50}$ from $10^{-4.72}$ M, CI$_{95}$=[$10^{-5.43}$ M, $10^{-4.07}$ M], to $10^{-3.41}$ M, CI$_{95}$=[$10^{-4.04}$ M, $10^{-2.75}$ M]. A corresponding pA$_2$ value was calculated which amounted to 8.28, CI$_{95}$=[6.8, 9.4].

Summarizing and interpreting the results of the in vitro ischemia model, GBP-L diminished the potentially neurotoxic [$^3$H]-Glu efflux, most probably through opening of K$_{ATP}$ channels in view of the high pA$_2$ of glibenclamide obtained.

Example 6

Experiments with GBP-L In Vivo

In vivo results were obtained in a rat model of pressure-induced retinal ischemia (Lagrèze et al. 1998). It was shown that neuronal loss caused by retinal ischemia is due to Glu release and its subsequent neurotoxic effects.

The method in brief: Retinal ischemia in the left eye was induced by elevating the intraocular pressure above systolic blood pressure for one hour. Retinal ischemia was confirmed by whitening of the fundus. In the first experiment 10 rats received 50 mg/kg GBP intraperitoneally immediately prior to ischemia and 50 mg/kg 6 hours after reperfusion, 10 rats received 50 mg/kg GBP-L i.p. immediately prior to ischemia and 50 mg/kg 6 hours after reperfusion, and 10 rats received vehicle alone. Ischemic damage was histologically quantified 14 days after ischemia: Both eyes were enucleated and immersed in 4% buffered formaldehyde for 24 hours. Retinal wholemounts were made and stained with cresyl violet, (0.1%, pH 4.5 for 30 min). Ischemic damage was quantified by counting the number of neurons in the ganglion cell layer in a masked fashion. This demonstrates retinal ganglion cells of a control eye in a high 400-times magnification. This control eye was not subjected to ischemia.

The dramatic decrease in the number of ganglion cells due to retinal ischemia are shown in Jehle et al. (2000). The percentage of surviving neurons was under 20%. The ischemic picture after intraperitoneal GBP corresponded exactly to that seen with pure ischemia. However, when GBP-L was given systemically the number of surviving neurons increased markedly (see FIG. in Jehle et al. 2000).

The quantification of all rectangles in all eyes of the 30 rats used were done by three observers in a blinded fashion: The examiners did not know which group had what drug.

Statistically, the ganglion cell numbers were evaluated as follows: In contrast to the usual ANOVA where the ratio of the mean squares between the treatment groups and the error mean square is used in the F-statistic, the nested design applied here requested another approach. Apart from the factor medication, there were three other sources of variation in our example, (1) the rat, (2) the eye, and (3) the replications of cell counting within each eye. To test for the medication effect the mean square for rat within medication has to be used as denominator. The variability of the eye is then contained in both the numerator (with all contributions to the variance) and the denominator (with the contributions to the variance except that of the factor medication). Thus, the variability of the eye is eliminated in the end and the variance of the factor medication is assessed appropriately in the F-test. The used model was: cell counts=med rat (med) eye(med*rat). The quantification yielded the result shown in FIG. 6.0.

The rate of surviving neurons under ischemia was 17.5%. The same rate was observed in the presence of gabapentin. The percentage of surviving neurons doubled in the presence of GBP-L. Thus, the direct measure for neuronal loss—the number of ganglion cell layer neurons—demonstrated a clear neuroprotective effect of GBP-L whereas GBP was ineffective.

K$_{ATP}$ Channels in Membranes of Cells or Mitochondria

The mode of action of GBP-L and GBP was tested with regard to mitochondrial K$_{ATP}$ channels (Szewczyk and Marban 1999). GBP-L was a potent activator of mitochondrial K$_{ATP}$ channels with a half-maximal depression of the mitochondrial membrane potential at 85 μM (for comparison: the IC$_{50}$ of diazoxide is 50 μM). Effects of GBP-L on the mitochondrial membrane potential were already seen at 5 μM. In contrast, GBP was hardly effective at the mitochondrial K$_{ATP}$ channel. Thus, the neuroprotective effect of GBP-L seems to be mediated predominantly through mitochondrial K$_{ATP}$ channels.

Regarding the non-ionic nature of GBP-L as compared to the zwitterion gabapentin, the action on mitochondrial K$_{ATP}$ channels may be facilitated by the higher lipophilicity and, therefore, membrane permeability of the drug.

Time-Effect Relationship

In order to evaluate the therapeutic window of GBP-L as an antiischemic drug (Pulsinelli et al. 1997) its time-effect relationship was tested at 75 mg/kg given twice prior to or after the end of ischemia with an interval of 6 hours. The experimental approach was the same as described above, except that another strain of rats was used (which may explain that in this trial pure ischemia did not depress the rate of surviving ganglion cells below 20%).

The time-effect relationship of GBP-L is shown in FIG. 7.0. Obviously, the neuroprotective action of GBP-L was maintained for more than three hours after recirculation.

Dose-Effect Relationship

The dose dependence of the neuroprotective effect of GBP-L was established using 25 mg/kg, 50 mg/kg and 75 mg/kg (see FIG. 7) given twice three hours and nine hours after the end of ischemia.

Thus, a dose-dependent effect can be assumed at the important time point of administration of three hours after recirculation.

Statistically, a regression line can be drawn through the individual data points yielding the following slope: 0.41, CI$_{95}$=[0.20, 0.61]. Since this slope is significantly higher than zero a real dose dependence is given.

These in vivo data on the time-and dose-effect relationship have been also published meantime (Lagrèze et al. 2001).

Summary

The observed depression of ischemia-induced [$^3$H]-Glu outflow by GBP-L is an important in vitro finding which, however, cannot explain the discrepancies between the in vivo effects of GBP-L and GBP. These in vivo results indicate a clear neuroprotective effect of GBP-L, but not of GBP, in a rat model of retinal ischemia. According to in vitro results on mitochondrial K$_{ATP}$ channels where GBP-L was a potent agonist, but GBP was not, the neuroprotective effect of GBP-L seems to be mediated predominantly through mitochondrial K$_{ATP}$ channels.

References

Bradford H F, Ward H K, Thomas A J (1978) Glutamine—a major substrate for nerve endings. J Neurochem 30:1453–1459.

Carter R J, Lione L A, Humby T, Mangiarini L, Mahal A, Bates G P, Dunnett S B, Morton A J (1999) Characterization of progressive motor deficits in mice transgenic for the human Huntington's disease mutation, J Neurosci. 19:3248–3257.

Davies S W, Turmaine M, Cozens B A, DiFiglia M, Sharp A H, Ross C A, Scherzinger E, Wanker E E, Mangiarini L, Bates G P (1997) Formation of neuronal intranuclear inclusions underlies the neurological dysfunction in mice transgenic for the HD mutation. Cell 90:537–548.

Freiman T M, Kukolja J, Heinemeyer J Eckhardt K, Aranda H, Rominger A, Dooley D J, Zentner J, Feuerstein T J (2001) Modulation of K$^+$-evoked [$^3$H]-noradrenaline noradrenaline release from rat and human brain slices by gabapentin: Involvement of K$_{ATP}$ channels. Naunyn-Schmiedeberg's Arch Pharmacol 363:537–542.

Knörle R, Assmann D, Landwehrmeyer G B, Scheremet R, Müller K, Feuerstein T J (1997) Aspartate, glutamate, glutamine, glycine and □-aminobutyric acid in human bioptic neocortical areas: comparison to autoptic tissue. Neuroscience Letters 221:169–172.

Jehle T, Lagrèze W A, Blauth E, Knörle R, Schnierle P, Lücking C H, Feuerstein T J (2000) Gabapentin-lactam (8-aza-spiro[5,4]decan-9-on, GBP-L) inhibits glucose oxygen deprivation-induced [$^3$H]-glutamate release and is a neuroprotective agent in a model of acute retinal ischemia. Naunyn-Schmiedeberg's Arch Pharmacol 362:74–81.

Lagrèze W A, Knörle R, Bach M, Feuerstein T J (1998) Memantine is neuroprotective in a rat model of pressure-induced retinal ischemia. Invest Ophth Vis Sci 39:1063–1066.

Lagrèze W, Müller-Velten R, Feuerstein T J (2001) The neuroprotective properties of gabapentin-lactam. Graefe's Arch Clin Exp Ophthalmol 239:845–849.

Lipton S A, Rosenberg P A (1994) Excitatory amino acids as a final common pathway for neurologic disorders. N Engl J Med 330:613–622.

Ratnaraj N, Patsalos P N (1998) A high-performance liquid chromatography micromethod for the simultaneous detenrination of vigabatrin and GBP in serum. Ther Drug Monit 20:430–434

Ross R W, Lau-Cam C A (1986) General reversed-phase high-performance liquid chromatographic method for the separation of drugs using triethylamine as a competing base, J Chrom. 370:403–418.

Perez Velazquez J L, Frantseva M V, Carlen P L (1997) In vitro ischemia promotes glutamate-mediated free radical generation and intracellular calcium accumulation in hippocampal pyramidal neurons. J Neurosci 17:9085–9094.

Pulsinelli W A, Jacewicz M, Levy D E, Petito C K, Plum F (1997) Ischemic brain injury and the therapeutic window. Ann N Y Acad Sci 835:187–193.

Szewczyk A, Marban E (1999) Mitochondria: a new target for K channel openers? Trends Pharmacol Sci 20:157–161.

McGowan D P, van Roon-Mom W, Holloway H, Bates G P, Mangiarini L, Cooper G J, Faull R L, Snell R G, 2000, Arnyloid-like inclusions in Huntington's disease. Neurosci 100:677–680.

Schinder, Alejandro, F., Olson Eric, C., Spitzer Nicholas, C., Montal Mauricio, The Journal of Neuroscience, Oct. 1, 1996, 16 (19): 6125–6133

Violante V, Luongo A, Pepe I, Annuziata S, Gentile V, Brain Res Bull 2001 October-November 1; 56 (3–4): 169–72

Additional advantages, features and modifications will readily occur to those skilled in the art. Therefore, the invention in its broader aspects is not limited to the specific details, and representative embodiments, shown and described herein. Accordingly, various modifications may be made without departing from the spirit or scope of the general inventive concept as defined by the appended claims and their equivalents.

As used herein and in the following claims, articles such as "the", "a" and "an" can connote the singular or plural.

All documents referred to herein are specifically incorporated herein by reference in their entireties.

Although only a few exemplary embodiments of the present invention have been described in detail in this disclosure, those skilled in the art who review this disclosure will readily appreciate that many modifications are possible in the exemplary embodiments (such as variations in sizes, structures, shapes and proportions of the various elements, values of parameters, or use of materials) without materially departing from the novel teachings and advantages of the invention. Accordingly, all such modifications are intended to be included within the scope of the invention as defined in the appended claims.

Other substitutions, modifications, changes and omissions may be made in the design, operating conditions and arrangement of the preferred embodiments without departing from the spirit of the invention as expressed in the appended claims.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All references cited herein, including all U.S. and foreign patents and patent applications, are specifically and entirely hereby incorporated herein by reference, including the priority documents. It is intended that the specification and examples be considered exemplary only, with the true scope and spirit of the invention indicated by the following claims.

The Priority Document, DE 197 51 062.0 is expressly incorporated herein by reference in its entirety.

What is claimed is:

1. A method for treating a polyglutamine disease selected from the group consisting of Huntington's disease, spino and bulbar muscular atrophy, dentatorubralpallidoluysian atrophy, spinocerebellar ataxia type 1, spinocerebellar ataxia type 2, spinocerebellar ataxia type 3, spinocerebellar ataxia type 4, spinocerebellar ataxia tyne 5, sninocerebellar ataxia type 6, and spmocerebellar ataxia type 7, comprising: administering to a subject in need thereof an effective amount of a pharmaceutical composition comprising: a pharmaceutically acceptable carrier and a pharmaceutically effective amount of a 2-pyrrolidinone derivative of the general formula

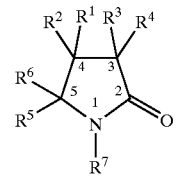

in which
R$^1$ and R$^2$ are, independently of one another, hydrogen atoms, hydroxyl groups, amino groups, C$_1$–C$_{10}$ alkoxy radicals, C$_1$–C$_{10}$ alkyl radicals or C1–C10 alkyl-amino radicals, or R$^1$ and R$^2$, together with the carbon atom in position 4 of the pyrrolidinone ring, form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, C$_1$–C$_4$ alkyl radicals, C$_1$–C$_4$ alkoxy radicals and C$_1$–C$_4$ alkylamino radicals, wherein R$^1$ and R$^2$ are not both hydrogen atoms, R$^3$, R$^4$, R$^5$, and R$^6$ are, each independently of one another, hydrogen atoms, halogen atoms, hydroxyl groups, amino groups, C$_1$–C$_{10}$ alkyl radicals, C$_1$–C$_{10}$ alkoxy radicals, C$_1$–C$_{10}$ alkylamino radicals or C$_6$–C$_{10}$ aryl radicals, and R$^7$ is a hydrogen atom or a C$_1$–C$_{10}$ aryl radical or C$_1$–C$_{10}$ acyl radical, or a pharmacologically acceptable salt thereof or prodrug thereof.

2. The method of claim 1, wherein said R$^3$, R$^4$, R$^5$, and R$^6$ radicals are hydrogen atoms.

3. The method of claim 1, wherein one of said R$^1$ and R$^2$ radicals is a hydrogen atom, and the other radical is a C$_1$ to C$_{10}$ alkyl radical.

4. The method of claim 1, wherein said R$^1$ and R$^2$ radicals form, together with the carbon atom in position 4 of the pyrrolidinone ring, a six-membered saturated hydrocarbon ring.

5. The method of claim 1, wherein said 2-pyrrolidinone derivative comprises 8-azaspiro[5,4]decan-9-one.

6. The method of claim 1, wherein said disease is Huntington's disease.

* * * * *